US005633349A

United States Patent [19]
Reichl

[11] Patent Number: 5,633,349
[45] Date of Patent: May 27, 1997

[54] METHOD OF INACTIVATING PRIONS (SLOW VIRUSES) CONVENTIONAL VIRUSES AND OTHER INFECTIONS AGENTS IN BIOLOGICAL MATERIAL

[76] Inventor: Herwig Reichl, Lagergasse 158, A-8020 Graz, Austria

[21] Appl. No.: 300,596

[22] Filed: Sep. 2, 1994

Related U.S. Application Data

[63] Continuation of Ser. No. 931,926, Aug. 18, 1992, abandoned.

[30] Foreign Application Priority Data

Aug. 19, 1991 [AT] Austria ................... 1629/91

[51] Int. Cl.⁶ .......................... C07K 14/435; G12N 7/06
[52] U.S. Cl. .................. 530/364; 530/380; 530/830; 435/238
[58] Field of Search ................... 530/364, 380, 530/830; 435/238

[56] References Cited

U.S. PATENT DOCUMENTS

| | | | |
|---|---|---|---|
| 4,314,997 | 2/1982 | Shanbrom | 424/101 |
| 4,540,573 | 9/1985 | Neurath et al. | 530/364 |
| 4,623,717 | 11/1986 | Fernandes et al. | 530/380 |
| 4,754,019 | 6/1988 | Gion et al. | 530/364 |
| 4,816,251 | 3/1989 | Seelich | 424/101 |
| 4,939,176 | 7/1990 | Seng et al. | 514/724 |
| 4,965,344 | 10/1990 | Hermann | 530/351 |
| 5,071,650 | 12/1991 | Dove et al. | 424/85.8 |
| 5,151,499 | 9/1992 | Kamayema et al. | 530/381 |
| 5,177,191 | 1/1993 | Brockway et al. | 530/383 |

FOREIGN PATENT DOCUMENTS

| | | |
|---|---|---|
| 0050061 | 4/1982 | European Pat. Off. . |
| 63-166835 | 7/1988 | Japan . |
| 9015613 | 12/1990 | WIPO . |

OTHER PUBLICATIONS

Micro–organisms, function form and environment, 2nd Edition Lilian E. Hawker and Alan H. Linton, pp. 132–133 (Edward Arnold, Ltd. 1979).

Negative Strand Viruses and the Host Cell, Edited by B. W. J. Mahy and R. D. Barry, pp. 29;34, 35 and 80 (Academic Press, 1978).

Dictionary of Microbiology and Molecular Biology, 2nd Edition, Paul Singleton and Diana Sainsbury, pp. 319–320 (John Wiley and Sons), 1987.

Prusiner et al., "Molecular Properties, Partial Purification . . . ," Biochemistry, vol. 19, pp. 4883–4891 (1980).

Diener et al., "Viroids & Prions", Proc. Natl. Acad. Sci., vol. 79, pp. 5220–5224 (1982).

Prusiner et al., "Scrapie agent contains . . .", vol. 78, (11) pp. 6675–6679. (1981).

Prusiner et al., "Thiocyanate & hydroxylions . . . ", Proc. Natl. Acad. Sci., vol. 78 (7), pp. 4606–4610, (1981).

Biochemistry Handbook of D. Voet and J. C. Vost (1990) p. 181 Merck Index, 10th Ed. Compound 9431, 1983.

Novel Proteinaceous Infectious Particles cause Scrapie, Prusiner Science, vol. 216, pp. 136–144 (1982).

Protein Denaturation, Charles Tanford, pp. 69, 173, 174 Advances Protein Chemistry, vol. 23 (1968) and vol. 24 (1969).

Pocchiari et al. Archives of Virology 98, pp. 131–135 (1988).

Pocchiari et al, Javma 196 (10) pp. 1683 to 1684 (1990).

Pocchiari, Developments in Biological Standardization, vol. 75, 00 87 –95 (1991).

Pocchiari, Developments in Biological Standardization, vol. 75, pp. VI to IX (1991).

*Primary Examiner*—Chhaya D. Sayala
*Attorney, Agent, or Firm*—Herbert Dubno; Jonathan Myers

[57] ABSTRACT

A method for the inactivation of prions, viruses and other infectious agents, which might be present in a biological raw material (e.g. plasma for the preparation of albumin), leaving the desired biological product (e.g. BSA, HSA) intact. To achieve this, the biological raw material is treated with a chaotropic agent, e.g. urea or siodium thiocyanate for approx. 18 hours. Before this, a detergent, e.g. sodium dodecyl sulfate, as well as ethanol or methanol can be added, and the solution can be heated to 70° C. and kept at this temperature for 30 minutes. After cooling and acidification, denatured globulins can be removed. By modifications of this process (e.g. different concentrations, pH-values, temperatures etc.) a wide range of biological products (serum, plasma, proteins, peptides, gangliosides etc.) can be treated and rendered free of viruses, prions and all other infectivity.

11 Claims, No Drawings

METHOD OF INACTIVATING PRIONS (SLOW VIRUSES) CONVENTIONAL VIRUSES AND OTHER INFECTIONS AGENTS IN BIOLOGICAL MATERIAL

This is a continuation of application Ser. No. 07/931,926 filed on 18 August 1992, now abandoned.

FIELD OF THE INVENTION

My present invention relates to a method of reliably inactivating prions (slow viruses), conventional viruses and other infectious agents (e.g. bacteria) during the production of proteins.

More particularly, the invention provides a virus inactivation process suitable for use in the preparation of Bovine Serum Albumin (BSA) from bovine plasma or serum.

BACKGROUND OF THE INVENTION

In the production of proteins from animal serum or tissue, there is the potential of contamination by infectious agents that may be present in the primary starting material. The problem is particularly complex when considering the hazards of Slow Viruses such as Bovine Spongiphorme Encephalopathy (BSE) and Creutzfeld-Jacob Syndrome (CJS) and, possibly, various unknown viruses.

Witness the recent tragic example of HIV infection of many people due to the consequences of blood transfusions. Much of this happened before the pathogenic agents of AIDS became well known and has now resulted in pre-screening of donors and the development of procedures to eliminate the HIV virus during the processing of sera and proteins. The more knowledge of the nature of the pathogenic agent is available, the easier it is to develop a suitable procedure to destroy it.

Historically, infectious agents such as bacteria, have well established methods of control that involve different forms of sterilization (e.g. steam sterilization, dry sterilization, pasteurization, sterile filtration, ethylene oxide sterilization, radiation inactivation, etc.). With viruses, there are also established methods which involve lowering of the pH to 4.0 or below, or use of organic solvents in high concentrations. Extended periods of heating at 60° C. also may be used. In addition, UV treatment, formaldehyde and specific antiviral agents have been employed. However, these techniques sometimes have adverse effects on the proteins being isolated.

For some years now, new and previously unknown species of pathogenic agents have appeared and have been reported in scientific publications. These have been referred to as prions. The structure of these prions has been the subject of intense investigation and different points of view have been expressed. Some scientists feel they are extremely small viruses, while most experts now feel that prions are actually infectious proteins without a DNA or RNA core. This is the first contradiction to the scientific theory that DNA/RNA is essential for the duplication of infectious agents. While there is no firm evidence on the exact structure of these prions, there are diseases that have been identified recently both in humans and animals, that appear to be attributable to prions. No successful therapeutic treatments have been developed and as a result these diseases are always fatal. Adding to the problem is the fact that the incubation period can be up to 30 years and this factor presents a major challenge to the scientists involved.

One of these diseases, BSE (Bovine Spongiphorme Encephalopathy), the mysterious English-origin cattle disease, is the focus of much attention. Another is Scrapie of sheep and goat which actually may be the source of the BSE disease.

In humans there are diseases such as Kuru (an illness occuring with the ritual cannibals in Papua, New Guinea), the Creutzfeld-Jacob Syndrome and the Gerstmann-Straeussler Syndrome. The occurrence of these exotic illnesses is still fortunately very low, probably occuring at 1:1,000.000 but there are striking similarities when compared to the Alzheimer-syndrome. However, BSE is now reported to have reached epidemic proportions in England and is caused by the use of rendered materials in cattle feed and can originate with Scrapie infected sheep. Dairy cattle, in particular are at the highest measurable risk. A tragically similar incidence has occurred with humans.

During the production of human growth hormone from human pituitary glands collected from cadavers, the pathogenic agent of Creutzfeld-Jacob Syndrome was introduced. Several cases have now been reported in patients treated with this growth hormone. The patients were predominantly children, whereas the disease normally attacks adults over 50 years of age.

These examples point out the potential danger of these new diseases and the difficulties in diagnosing and treating them effectively.

The prions have very little, if any, nucleic acid and the prion protein is encoded by the host gene and is later transformed into a pathogen. Prions do not produce immune responses and the absence of antibodies makes diagnosis even more difficult. Prions are extremely resistant to physical and chemical methods of destruction. High concentrations of mineral acids or bases and preferably at high temperatures, Alkaline hypochlorite in high concentration, and temperatures above 150° C. can eliminate prions. Mowever, these conditions effectively destroy or inactivate any biological properties of the native proteins as well. In order to produce a biological material that guarantees the absence of prions, conventional viruses and other infectious agents, a combination of inactivation methods appears to be necessary and must be supported by a biological test method to show that any infectious agents present (or deliberately added as controls) are definitely destroyed. Screening of the primary material is not a possibility as there is no known method to detect prions easily. Similarly, collecting the primary materials from areas where the disease has not been detected is not satisfactory when one considers the possible incubation period of up to 30 years.

A biological test system has been developed, where the material to be tested is injected into the brains of mice and the mice are then observed for pathological symptoms for up to 2 years. This method is impractical as a screening method for starting materials or as a batch testing method in production control. It can be used as a validation method of a new manufacturing process where prions are deliberately added to the starting material. However, safety precautions must be observed and the test animals must be maintained and tested in special P3 laboratories.

OBJECTS OF THE INVENTION

It is, therefore, the principal object of the invention to provide an improved method of destroying prions, especially in association with the production of protein and without damage to the protein whereby drawbacks of prior art methods are abviated.

Another object is to provide an improved method of producing protein-containing biologicals free from prions and other viral or bacterial agents.

DESCRIPTION OF THE INVENTION

According to the invention the biological material is contacted with a chaotropic reagent, usually 6–8 molar urea or 1–2 molar sodium thiocyanete, for a minimum of 12 hours, preferably a minimum of 18 hours at a temperature of 20°–25° C.

The invention is thus a manufacturing process for biologicals of human or animal origin which inactivates or eliminates any prions or other infectious agents that might exist in or have been added to the starting material. This can be demonstrated using BSA (bovine serum albumin) as an example. Prior to production, starting material such as bovine plasma was inoculated with the brain homogenate of Scrapie infected mice. After processing of the plasma under P3 laboratory conditions, the BSA was freeze-dried and this was injected into the brains of susceptible mice. Positive and negative controls were included. The mice were observed for pathological signs of disease and as further proof, a brain homogenate from each mouse was injected into a series of mice. The processing procedure that has been developed allows the production of a virus free (and BSE/Scrapie free) biological products for a wide range of applications in many areas.

This invention achieves the reliable destruction of prions and any conventional viruses that might exist in biological material, without damaging or destroying this material. This is done by treating the biological material with the chaotropic reagent for at least 12 hours, preferably 18 hours.

In my research I have found that prions can be eliminated by extended treatment with the chaotropic reagent at average room temperature (20°–25° C.). By such a treatment proteinaceous biological materials (e.g. albumins) are not irreversibly denatured, whereas viruses and bacteria are reliably destroyed.

As the chaotropic reagent, either 6–8 molar urea, in relation to the total quantity, or 1–2 molar sodium thiocyanate, again in relation to the total quantity, can be used. Either can be removed by means of dialysis, diafiltration or gel permeation chromatography after treatment.

In order to improve reliability or elimination of the germs it is advisable, before treating the biological material with the chaotropic reagent and possibly after diluting it with sterile and pyrogen free water, to adjust the biological material to pH 6.5 and add about 1 g/l of a preferably anionic detergent.

As a detergent any alkyl sulfate or its derivatives, preferably a $C_8$ to $C_{26}$ -alkyl sulfate such as sodium dodecyl sulfate (SDS), and/or a sarcosinate, preferably sodium -(N-lauroyl) sarcosinate and/or any alkyl sulfonate, e.g. a $C_8$ to $C_{26}$ -alkyl sulfonate or a derivative thereof or any mixture of these can be used. pH is adjusted by addition of diluted hydrochloric acid. It is advisable to add to the detergent 8–10% (v/v) methanol or ethanol. After addition of detergent and alcohol, it is advisable to heat the biological starting material slowly to 70°–75° C. under stirring and keep it at this temperature for a minimum of 5 and preferably for at least 15, better, 30 minutes. After this it can be cooled, its pH be adjusted to 3 to 4.5, and denatured globulins can be removed.

Bovine Serut Albumin (BSA) was chosen as an example for testing of the invention, firstly, because it is used in large quantities, secondly, because bovine primary material is being threatened by BSE and thirdly because the human analog Human Serum Albumin (HSA) is a very important therapeutic material. The procedure can be applied directly (without any alteration) to HSA production. For other proteins of animal as well as human sources it can be modified, as already has been demonstrated with serum and IgG. The procedure, as applied to BSA, can be described as follows:

Plasma or serum from which BSA or HSA is to be made, is diluted with water, pH is adjusted to 6.5, ethanol or methanol are added to 8–10% (v/v), and a strong tenside, preferably SDS or sodium (N-lauroyl) sarcosinate at 1 g/l is added. The solution is heated to a temperature of 70° C. and stirred at this temperature for about 15–30 min.

Afterwards the material is cooled down quickly, the pH adjusted to 4.0 to 4.2, the globulins that have precipitated are separated and the clear solution is neutralized using dilute sodium hydroxide solution.

Then a chaotropic reagent (at high concentration) is added, preferably 6–8 molar urea or 1–2 molar sodium thiocyanate. The solution is kept at room temperature for 16 hours, then the reagent is removed by chromatography, dialysis or diafiltration. The desalted solution is then concentrated. Additives may be added.

Ultrafiltration can be used as the best method of concentration. Then the solution is either sterile filtered and sterile filled or dried, preferably freezed-dried. Thermal after-treatment of the solution ("Pasteurization" in the presence of stabilizers) or of the powder (steam-injection) can then be used as an optional step. Instead of serum or plasma, any other primary material containing albumin can be used, e.g. placental blood, different fractions of cohn plasma fractionation and so on.

SPECIFIC EXAMPLES

Effectiveness of the procedure outlined here has been shown using the following test models:

Scrapie prions were added to plasma which was subjected to this process. The resulting albumin solution was injected into the brains of susceptible mice. High concentrations of conventional viruses (Bovine Viral Diarrhoea—BVD, Infectious Bovine Rhinotracheitis—IBR, Parainfluenza 3—PI3, Foot and Mouth Disease—FMD, Maedi-Visna Virus—MVV, and Parapox Virus of Sheep—ORF) were added to bovine plasma. Then albumin solution was processed according to the outlined procedure. These solutions Were autosterile, which proves the complete destruction of bacteria, and neither scrapie nor any viral infectivity could be seen in appropriate test systems.

Treatment procedure: 3 g dried bovine plasma (equals 2 g protein) were dissolved in 35 ml distilled, sterile water. 4 ml ethanol (100%) were added. The pH was adjusted with diluted hydrochloric acid to 6.5, and 45 mg (=0.1%) sodium dodecyl sulphate (purity>95%) were dissolved.

There was a total volume of 44 ml. Under the necessary safety precautions (P3 facilities, Laminar Flow Hood . . . ) 225 µl of a 20% Scrapie-Brains-Homogenate (Titer: $2\times10^9$ $LD_{50}/g$) were added and homogenized, or high concentrations of virus solutions (see Table 1). The solution was put in a 70° C. water bath, after 10 min the solution itself reached 70° C. and was kept at that temperature for 30 min. After every 10 min a magnetic stirrer was actuated for 1 min. After the incubation period the material was put on ice and in this way cooled down. The cold solution was homogenized again after having adjusted the pH to 4.2 with 200 µl of hydrochloric acid (5%).

Removal of the precipitated globulins was done at 6000 rotations per min (equals 4000×g) at a temperature of 4° C. for 10 min. The clear supernatant was decanted. It was a pure bovine albumin solution with a volume of 20.5 ml. The solution was neutralized by addition of 250 µl of sodium hydroxide (5%). Then 15 g urea were added, increasing the volume to 30 ml resulting in a concentration of 8 molar. This solution was kept at room temperature (21° C.) for 16 hours. The urea was removed by means of gel permeation chromatography: 15 g of Sephadex G 50 (Pharmacia, Uppsala) 5 were heated in 500 ml sterile and distilled water and left overnight. The soaked gel was filled into an acrylic column (5 cm diameter, 30 cm height) and washed with sterile, distilled water (200 ml). The flowrate was 7.5 ml/min. 30 ml of the above solution were applied, then the column was washed with 100 ml water. Two fractions were collected: 50+40 ml. After that no protein could be detected. The 90 ml were lyophilized and yielded 0.7 g Bovine Serum Albumin. Alternatively, in some experiments the urea used was removed by means of diafiltration (Amicon S-1 modul, cut-off 10,000 d). In these procedures diafiltration was done with about 1000 ml distilled water, then the solution was concentrated to about 50 ml and finally it was lyophilized.

Biological testing for SCRAPIE/BSE: This albumin (procedure above) was dissolved in 3 ml physiological sodium chloride solution and injected into the brains of mice in aliquot quantities of 20 µl. Total number of mice: 136. The mice were used C57/B16. As positive control a serial dilution of the scrapie inoculum was used (see above, $2 \times 10^9$ $LD_{50}$/g), 8 stages of dilution. As negative control BSA solution (procedure above) was prepared without the scrapie inoculum. All inoculations were done at 12 animals each, i.e. in 12 fold repetition.

Result: Titer in positive control was confirmed. No symptoms of disease or death cases in negative control and trial group.

Biological testing for conventional viruses: The BSA was dissolved in tissue culture medium used for those mammalian cells that can function as host cells for the respective virus. Positive (virus-strain-solution) and negative (pure medium) controls as well as test for unspecific cytopathogenity of albumin completed these test series.

Results: Not a single infectious virus particle survived in any of the virus strains tested. The data guarantee destruction rates of $>10^6$ (>1 Million) as a consequence of the respective procedure. Much higher clearance rates can be expected, as the infectious titer of the starting material had been limiting in all cases tested.

The equivalence of N-lauroylsarcosinate and sodium dodecyl sulfate as a detergent useful for the preparation of BSA from plasma was demonstrated in a similar experiment, but without spiking with infectious material. Parameters checked were yield and purity of BSA (>98% for both detergents). The equivalence of urea and sodium thiocyanate as chaotropic reagents was tested and demonstrated using RNP (ribonucleoprotein)—particles of Influenza Virus (a model for nucleic acid—protein interactions) and using affinity chromatography models (e.g. with gelatine-fibronectin).

TABLE 1

| Infectious agent | initial conc. | Test system | residual infectiv. | clearance rate |
|---|---|---|---|---|
| Scrapie/BSE | $2 \times 10^8$ | Mouse C57/B16 | 0 | $>10^7$ |
| BVD Virus Strain "Singer", pass. 9 | $1 \times 10^8$ | BHK | n.d. | $3 \times 10^6$ |
| IBR Strain "Ames", pass. 18 | $1.8 \times 10^6$ | BHK | n.d. | $7 \times 10^4$ |
| PI 3 Strain "Freistadt", pass. 78 | 80 HTH units | ? | n.d. | ? |
| MKS 0 1 BFS 1860, pass. 5 | $2 \times 10^7$ | MDCK | n.d. | $1 \times 10^6$ |
| MVV (ATCC-VR-779) | $1.2 \times 10^9$ | WSCP | n.d. | $3 \times 10^6$ |
| ORF (Dept. Pathol., Glasgow) | $2 \times 10^9$ | PAL-6 | n.d. | $3.4 \times 10^6$ |

BSE = Bovine Spongiphorme Encephalopathy
BVD = Bovine Viral Diarrhoea
IBR = Infectious Bovine Rhinotracheitis
PI3 = Parainfluenza 3
MVV = Maedi-Visna Virus
ORF = Parapox Virus Of Sheep
MKS = Foot and Mouth Disease.

I claim:

1. In a process for treating a biological or biogenic material derived from serum or plasma and containing an infectious agent, the improvement which comprises destroying prions in said biological or biogenic material by treating the biological or biogenic material with urea or a thiocyanate as a chaotropic agent for a minimum of 12 hours at a temperature of 20° to 25° C. and removing the chaotropic agent from the biological or biogenic material following the treatment.

2. The improvement defined in claim 1 wherein urea in a concentration of 6 to 8 molar is used as the chaotropic agent.

3. The improvement defined in claim 1 wherein sodium thiocyanate in a concentration of 1 to 2 molar is used as the chaotropic agent.

4. The improvement defined in claim 1 wherein the urea or thiocyanate is removed after treatment of the biological or biogenic material to destroy prions by dialysis, diafiltration or gel permeation chromatography.

5. A process for treating a biological or a biogenic material derived from serum or plasma and which contains an infectious agent, said process comprising, in the following sequence, the steps of:
 (a) adjusting the pH of the biological or biogenic material to about 6.5 and adding thereto 1 g/l of an anionic detergent;
 (b) slowly heating the biological or biogenic material to a temperature of 70° to 75° C. with stirring and keeping said biological or biogenic material at this temperature for a minimum of 15 minutes; and thereafter (c) treating the biological or biogenic material with urea or a thiocyanate as a chaotropic agent for a minimum of 12 hours at a temperature of 20° to 25° C. to destroy prions, and removing the chaotropic agent from the biological or biogenic material following the treatment.

6. The process defined in claim 5 wherein the biological or biogenic material is diluted in step (a) with sterile pyrogen-free water.

7. The process defined in claim 5 wherein an alkyl sulfate, a sarcosinate or an alkyl sulfonate is used as the detergent.

8. The process defined in claim 5 wherein the pH is adjusted with dilute hydrochloric acid.

9. The process defined in claim 5 wherein 8 to 10% (v/v) of methanol or ethanol is added to said biological or biogenic material.

10. The process defined in claim 5 wherein in step (b) after heating the biological or biogenic material is cooled, acidified to a pH of 4 to 4.2 and precipitated globulins are removed.

11. The process defined in claim 5 wherein, in step (b), the biological or biogenic material is kept at 70° to 75° C. for a minimum of 30 minutes.

* * * * *